United States Patent [19]

Crytzer et al.

[11] Patent Number: 5,327,083
[45] Date of Patent: Jul. 5, 1994

[54] METHOD AND APPARATUS USING MAGNETIC FLUX SCANNING TO TEST GRAIN STRUCTURE OF MAGNETIC SHEET MATERIAL

[75] Inventors: Layton D. Crytzer, Natrona Heights; Leroy R. Balmer, Saxonburg, both of Pa.

[73] Assignee: Allegheny Ludlum Corporation, Pittsburgh, Pa.

[21] Appl. No.: 854,030

[22] Filed: Mar. 19, 1992

[51] Int. Cl.⁵ ................... G01N 27/72; G01R 33/12
[52] U.S. Cl. ............................. 324/239; 324/262
[58] Field of Search ............ 324/235, 234, 225, 226, 324/227, 228, 239-243, 232, 222, 224, 262

[56] References Cited

U.S. PATENT DOCUMENTS

| | | | |
|---|---|---|---|
| 1,322,405 | 11/1919 | Burrows | 324/240 |
| 2,103,224 | 12/1937 | Schweitzer et al. | 324/240 |
| 2,617,854 | 11/1952 | Van Valkenburg | . |
| 3,437,917 | 4/1969 | Gunkel et al. | 324/240 X |
| 3,706,028 | 12/1972 | Otala | 324/239 |
| 4,079,312 | 3/1978 | Osborn et al. | 324/226 |
| 4,250,451 | 2/1981 | Slagle | 324/239 |
| 4,394,193 | 7/1983 | Gifrerer | 324/222 X |
| 4,445,088 | 4/1984 | Schübel | 324/240 X |
| 4,510,447 | 4/1985 | Moyer | 324/240 X |
| 4,531,091 | 7/1985 | Kusenberger et al. | 342/242 |
| 4,602,212 | 7/1986 | Hiroshima et al. | 324/240 X |
| 4,675,604 | 6/1987 | Moyer et al. | 324/240 X |
| 4,686,471 | 8/1987 | Morita et al. | 324/227 X |
| 4,893,510 | 1/1990 | Ichikawa et al. | 73/620 |
| 4,931,730 | 6/1990 | Olsen et al. | 324/232 X |

FOREIGN PATENT DOCUMENTS

| | | |
|---|---|---|
| 238209 | 9/1987 | European Pat. Off. . |
| 469158 | 2/1992 | European Pat. Off. . |
| 0180355 | 10/1984 | Japan ................ 324/214 |

OTHER PUBLICATIONS

Taylor, *Soft Magnetic Materials* 10 Conference, Sep. 1991 "An On-Line Grain Size Measuring System for Electrical Steels Production", pp. 34.

*Primary Examiner*—Gerard R. Strecker
*Assistant Examiner*—Warren S. Edmonds
*Attorney, Agent, or Firm*—Patrick J. Viccaro

[57] ABSTRACT

The grain structure of electrical steel strip is tested by inducing a magnetic flux field into the strip by pole pieces at opposite sides of a permanent magnet. A magnetic detector head between the pole pieces responds to the leakage of flux as the steel strip and/or magnetic detection undergoes relative movement. A recorder is used to identify banding and mixed grain structures which cause a smaller flux leakage amplitude than larger desired grains.

19 Claims, 6 Drawing Sheets

METHOD AND APPARATUS USING MAGNETIC FLUX SCANNING TO TEST GRAIN STRUCTURE OF MAGNETIC SHEET MATERIAL

BACKGROUND OF THE INVENTION

1. Field of the Invention

This invention relates to a magnetic flux scanning method and apparatus for examining the grain structure of an electrically conductive metallic workpiece and, more particularly to the use of a magnetic field for detecting sites where there are a concentration of small grains in an electrical steel sheet product, such as a silicon steel.

2. Description of the Prior Art

The desired electrical properties for electrical steels are the result of a special manufacturing techniques including melting, rolling and heat treating procedures to establish relatively large grains with a very little dispersion of small grains in the final texture annealed silicon steel strip. Specific grain structure is developed and refined to impart desired electrical properties to the steel strip. Conventional grain oriented silicon steel has a typical grain size on the order of 3 to 5 mm and high permeability grain oriented steel on the order of 10-15 mm. Sometimes occurrences, such as inclusions of impurities or rolling and heat treating process deviations, may allow non-uniform grains to develop across the width and length of the strip. In particular, for example, a concentration of small grains or a mixture of large grains with many small grains and/or orientation of grains exhibit magnetic flux boundaries caused by the grain boundaries. As a result, there exists unwanted flux barriers that downgrade the intended electric properties. Not only may the grain size vary appreciably, but also there are poor qualities of material that appear as coarsened primary grains known as "banding". It is desirable to locate and accurately identify the unacceptable sites of banding and mixed grains structure so that bad material can be sheared, cut or otherwise extracted from the metal strip.

In U.S. Pat. No. 4,079,312 there is disclosed a testing apparatus for determining magnetic characteristics for a strip of moving material. A flux inducing and pick-up device is used for measurement of the flux induced into the strip of moving material. A magnetization coil is used to induce magnetic flux into the strip, two flux pick-up coils are arranged to respond to different flux characteristics at about the same area of the strip. Voltage outputs corresponding to the two different characteristics are processed in an electrical circuit to derive an output signal according to a mathematical formula. Such a continuous strip testing device is well suited to identify that poor quality magnetic properties of the strip exist within a broad area. However, this testing procedure can not be used to identify the specific site or nature of the deficient magnetic properties. Particularly important is the fact that the device can not differentiate between banding or mixed grain structures in silicon steel. It has been found that for silicon steel strip, banding and mixed grain structure can occur in very small sections, but those sections may be known to exist only generally within a broad area of a strip through the use of the device shown in the aforesaid U.S. Pat. No. 4,079,312.

Others have attempted to develop an on-line grain size measuring system for electrical steel production. Particularly, an ultrasonic device is suggested in U.S. Pat. No. 4,893,510 to measure a distribution of crystal grains in a metal sheet. An estimate is made of grains orientation based on the estimate of the magnitudes of amplitude of interferant multiple reflected waves. The frequency of bursts of ultrasonic pulses is related to the sheet-thickness and applied in the direction of the sheet thickness to obtain the reflected waves.

What is needed is a device that can locate and identify irregularities that exist in the grain structure on a continuous basis on a production line at strip speeds of 100 to 450 feet per minute (30.48 to 137.16 meters/min.). It is also desirable that such a device be useful in conjunction with other continuous strip testers, such as for measuring magnetic properties, to better understand the irregularities in the grain structure and the quality of the electrical sheet product.

Therefore an object of the present invention is to provide a flux scanning procedure and device to locate, identify the severity, and differentiate between banding and mixed grain structures in a grain oriented silicon steel strip.

SUMMARY OF THE INVENTION

According to the present invention there is provided an apparatus sensitive to various grain structures of an electrically conductive steel strip, the apparatus including the combination of: means for inducing a magnetic flux field to a detection site at one side of the steel strip, means for causing relative movement between the means for inducing a magnetic flux field and the steel strip to allow continuous examination of the grain structure at diverse sites, and means responsive to the flux leakage at grain boundaries in the steel strip for deriving an electrical signal indicative of the grain structure of the steel strip at selected detection sites established by the flux field.

According to the present invention there is also provided a method for identifying banding and mixed grains in a silicon steel strip, the method including the steps of inducing a magnetic flux field in the steel strip, causing relative movement between the magnetic flux field and the grain structure of the steel strip to allow continuous examination of the grain structure at diverse sites, producing an electrical signal corresponding in magnitude to leakage of magnetic flux, and comparing the magnitude of the voltage output represented by the magnetic flux leakage within areas of the steel strip having larger grains as compared with areas of the steel strip having smaller grains to determine areas of banding and mixed grain structure.

BRIEF DESCRIPTION OF THE DRAWINGS

These features and advantages of the present invention as well as others will be more fully understood when the following description is read in light of the accompanying drawings of which.

DETAILED DESCRIPTION OF THE PREFERRED EMBODIMENTS

Figure 1:
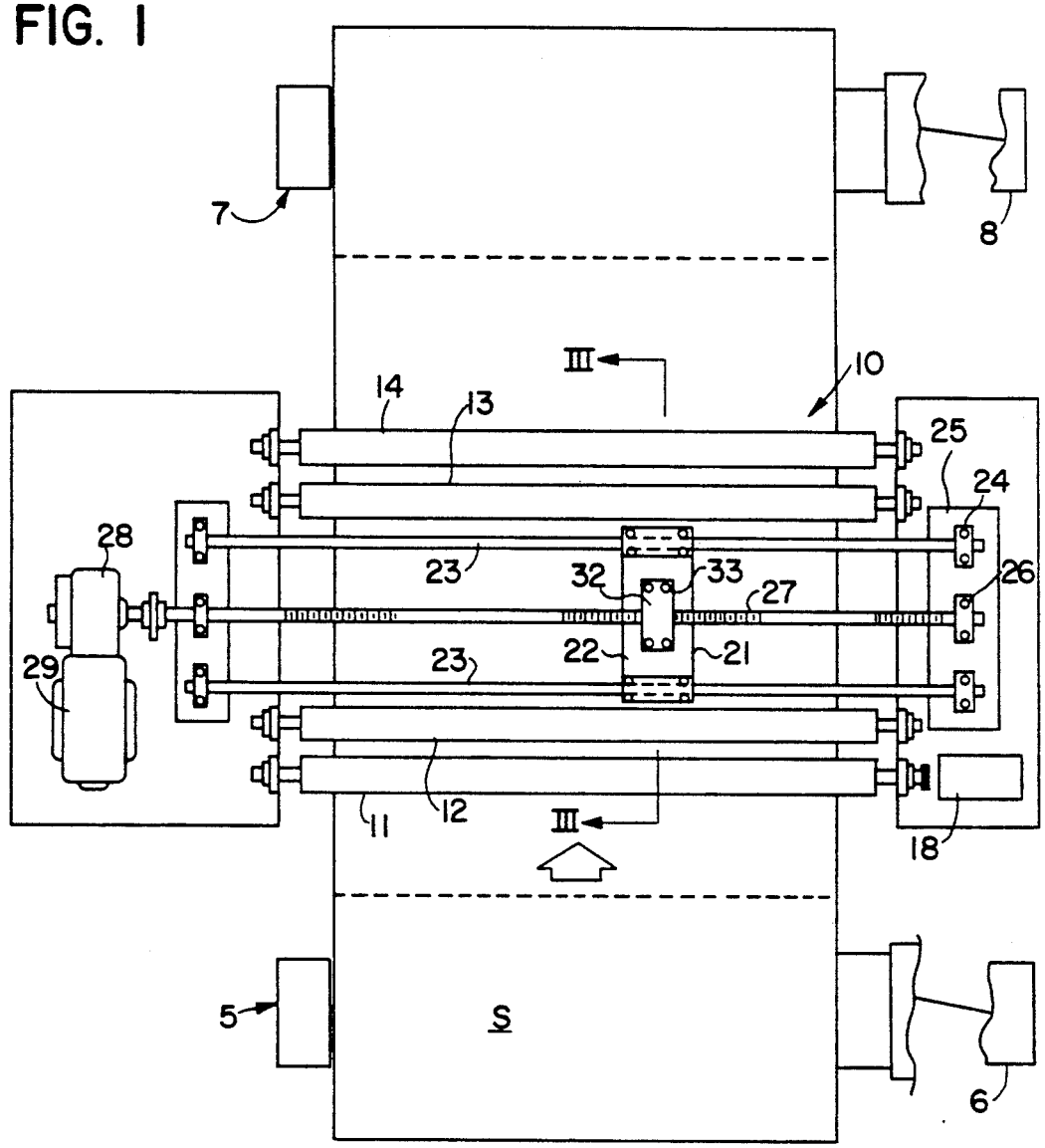
FIG. 1 is a plan view of apparatus for flux scanning magnetic sheet according to the present invention which is also useful to carry-out the method thereof.
Figure 2:
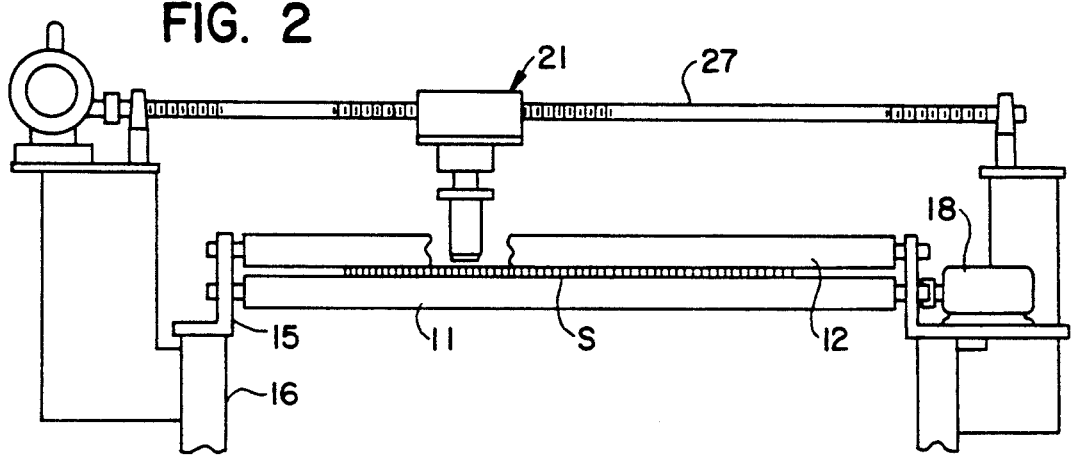
FIG. 2 is an elevational view of the apparatus shown in FIG. 1.
Figure 3A:
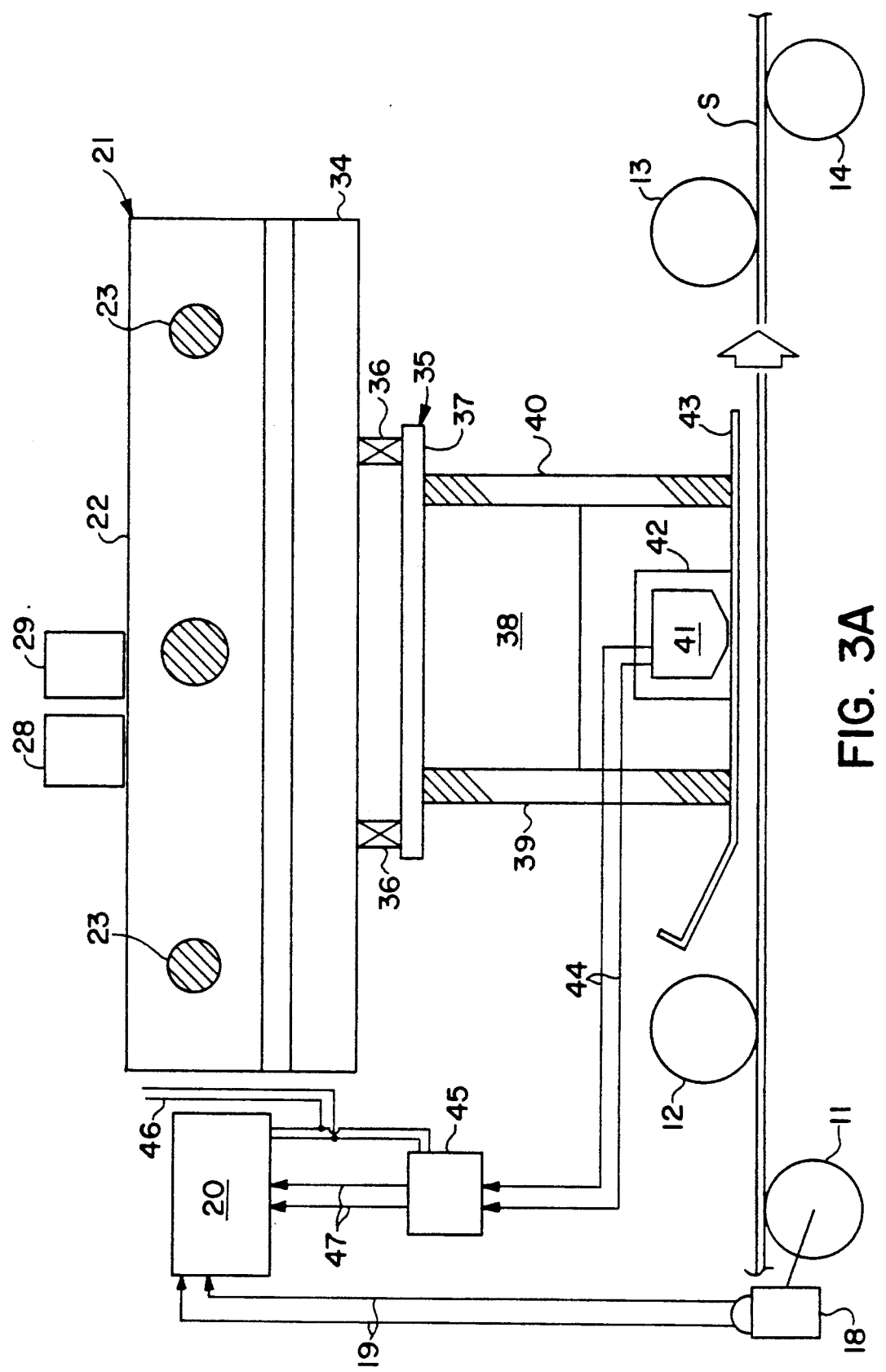
FIG. 3A is an enlarged sectional view taken along lines III—III of FIG. 1.

In FIGS. 1, 2 and 3A there is illustrated flux scanning apparatus 10 for scanning a strip S of magnetic material, typically, a silicon steel strip. The strip material is supplied to the device 10 by suitable facility including a payoff reel 5 rotatably controlled by a drive including a motor 6. After the strip passes through the device 10, it is again placed in coil form by a take-up mandrel 7 rotatably controlled by a drive including a motor 8. The payoff reel and take-up mandrel are per se well known in the art. Other equipment and operations may be conducted in line with the device 10 between payoff reel 5 and take-up mandrel 7.

The strip S is advanced along a pass-line transverse to the direction of movement by a scanning head 21 of the flux scanning apparatus 10 while the strip is supported and stabilized by a series of rollers. Such rollers may include entry lower and upper rollers 11 and 12, respectively, at the entry side of the flux scanning apparatus and delivery lower and upper rollers 14 and 13, respectively, at the discharge side of the flux scanning apparatus. The rollers may be supported in a conventional manner at their opposite ends by bearing assemblies that are in turn supported by housing members 15 carried on upstanding frame supports 16. Such rollers may be driven or non-driven rollers. At the entry side, as best shown in FIG. 3A, the strip advances along a pass line with roller 12 situated to rotate about a longitudinal axis above the pass line while roller 11 is situated to rotate about a longitudinal axis below the pass line. The rollers 11 and 12 are positioned relative to the pass line so that as the strip advances it drives both of the rollers to rotate about their respective longitudinal axis. Roller 11 has an extension to its arbor support shaft which is connected by a coupling to a pulse generator 18 that produces a pulse output corresponding to a measure of rotation by roller 11. The pulse output from the transmitter 18 is supplied by lines 19 to the chart recorder 20 to synchronize the chart speed to the strip speed. The pulse output may be supplied other conventional recording means, including a computer.

The scanning head 21 is traversed in a direction transversely to the direction at which the strip material is advanced by rollers 11, 12, 13 and 14. As the strip S passes beneath the flux scanning device 10, the scanning head is transported to and from across the top of the strip in a closely spaced apart relation for achieving a continuous random sampling of the strip edge to edge thereof. The scanning head 21 includes a guide block 22 slidably supported by spaced apart rods 23 (FIG. 3A). Each rod is supported at its opposite ends by a mounting block 24 that is in turn supported on pedestals 25 carried by the frame support 16. As shown in FIGS. 1 and 2, the rods 23 extend in a spaced apart parallel relation between which there is also rotatably supported by bearing blocks 26, a lead screw 27. The lead screw has a threaded portion that is rotated about a longitudinal axis by a gear drive 28 coupled to a drive motor 29. The lead screw 27 threadedly engages a feed nut 32 which is held by fasteners 33 to guide block 22. The guide block 22 is constrained to only linear movement by the guide rods 23 as the block traverses across the strip S. Secured to the underside of the guide block is a mounting plate 34 to which there is attached a sensing head unit 35 by support springs 36. The sensing head unit includes a top carrier plate 37 that supports a magnetic assembly 38 having at opposite ends thereof depending pole pieces 39 and 40.

The magnet 38 preferably is a permanent magnet for supplying a direct current (DC) flux field. Magnet 38 preferably is comprised of a plurality of permanent magnet plates arranged in a laminate fashion. In the alternative, the DC field could be supplied by transforming an alternating current supply. The pole pieces are spaced apart by a distance that allows the positioning therebetween of a magnetic pick-up head 41 for support by a carrier and magnetic shielding bracket 42. In this embodiment, the pole pieces 39 and 40 support a cover plate 43 which protects the magnetic pick-up head 41 from unwanted impingement with the strip particularly in the event of vertical vibrations and lap joints of the sheet or strip as it travels along the passline between rollers 12 and 13.

The electrical output signal produced by the magnetic pick-up head 41 is delivered by lines 44 to a preamplifier 45. Amplifier 45 receives a source of electrical power by supply lines 46 which also delivers electrical power to the recorder 20. The output from preamplifier 45 is delivered by lines 47 to recorder 20. As can be seen from FIG. 3A, an air gap or standoff distance exists by the spacing of the pick-up head 41 a short distance above the top surface of the strip. Typically, an air gap that is usually $\frac{1}{8}$ inch or less in height is chosen to allow the pick-up head to respond to the leakage of magnetic flux caused by the boundary surfaces of the grain structure of the strip. Movement of the sensing head unit, and in particular the leakage of magnetic flux from the flux field imparted to the strip by the pole pieces, is caused by boundary surfaces of grains. When the grain structure is relatively large, flux leakage signals are higher in magnitude as compared with the flux leakage when the grain structure is very small as, for example, when encountering banding in the steel strip. Thus, the flux leakage magnitude is much smaller when the banding occurs at the site where the flux field is intercepted by relative movement of a multitude of small grain boundaries.

It has been found that the magnetic pickup head 41 can be one commercially available, such as certain recording heads for audio equipment. Such heads generally have high relative sensitivity in order to respond to the high frequency of grain boundaries detected. The head 41 should be of relatively high inductance. Although actual inductance level does not appear critical, it has been found that an inductance of about 0.75 henry, or about 1 henry is suitable. Such high inductance provides electrical signals with less noise and distortion, i.e., "cleaner" signals. Audio magnetic heads having inductance ranging from 0.50 to 1.0 henry are generally available. Such magnetic heads will generate only a low voltage signal on the order of 12 millivolts or less under the circumstances of the present invention. If sensitivity and inductance are too low, then the output signal by the magnetic head will be unusable. For that reason a preamplifier 45 is used. The pickup head 41 should be maintained in a non-contacting relation to the moving strip S in order to minimize wear and tear associated with contacting devices on a rapidly moving strip.

Figure 3B:
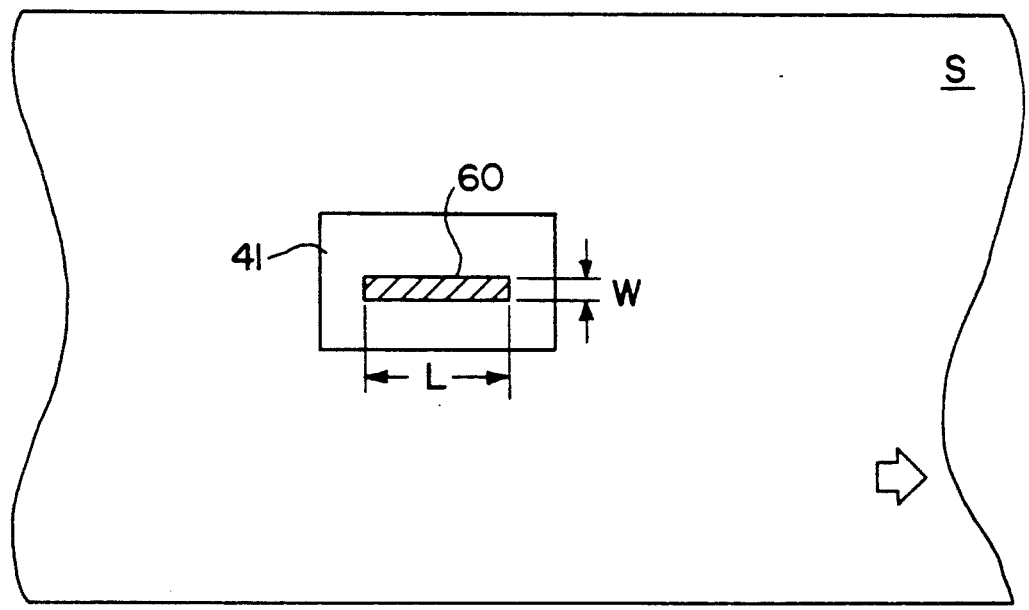
FIG. 3B is a plan view diagram of a pickup head of the present invention.

It was unexpectedly found that such a magnetic pickup head was capable of detecting magnetic flux leakage from the grain boundaries of the moving strip from a stand-off distance. Such commercially available heads are conventionally used by contact with the magnetic tape of recording devices. In a preferred embodiment, the head 41 is used by orienting it 90° to the conventional position used as magnetic recording head for audio devices. In order to better understand the importance of the orientation of the pickup head 41, the plan view of FIG. 3B shows the pickup area of the head relative to the moving strip or sheet. Within head 41 in close proximity to the moving strip S is a magnetic flux pickup area 60 having a length, L, and width, W. The length L is oriented in the direction of strip movement and the width W is oriented transverse to strip movement. It has been found that the length L is preferably about the same size or larger than the nominal grain size in good quality silicon steel having uniformly developed grain structure. It has been further found that the length L must not be smaller than the nominal grain size. Furthermore, the width W must be smaller than the length L, and preferably the width W is as small as possible. A pickup head 41 has worked well on conventional grain oriented steel in accordance with the present invention having a width W on the order of 3 to 4 microns and a length L of the order of 6 to 7 mm.

Figure 4A:
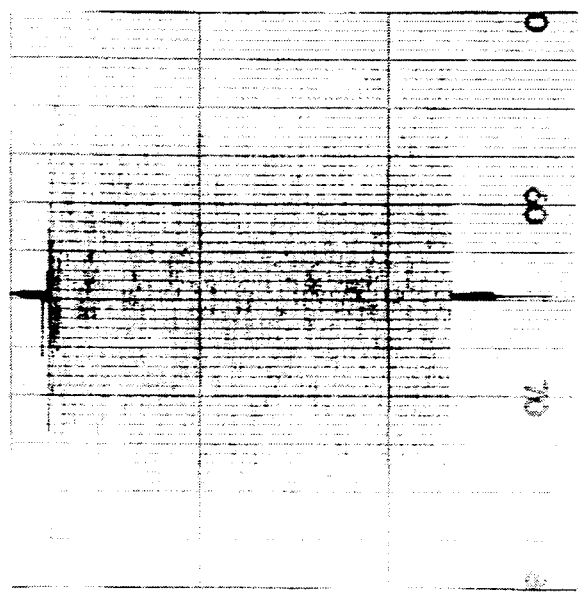
FIGS. 4A and 4B are recorder traces showing readouts of the flux scanning apparatus of the present invention.
Figure 4B:
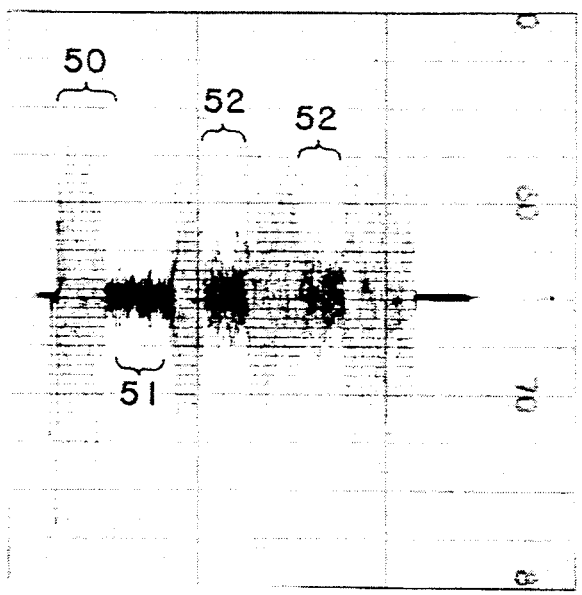

In order to maintain a high frequency response for the flux scanning according to the present invention, the device for recording must operate at a high speed and with a high resolution. FIGS. 4A and 4B are recorder traces obtained by the present invention on a process line with the test strip moving at approximately 300 feet per minute (91.5 meters/min.). A high speed thermal writing recorder was utilized to maintain the frequency response of the system and to accentuate the low amplitude (poor quality) signals by darkening the trace. The recorder traces represent a continuous scanning of flux leakage at grain boundaries within an area established by the required strip movement relative to the magnetic pickup head 41. FIG. 4A is a typical trace from a medium grain size in the strip on a single scan across the width of the moving strip. The consistent and large amplitude of this trace is indicative of uniform grain size and emphasizes the absence of banding or mixed grain structures. In FIG. 4B there are three (3) distinctive trace portions indicative of variations to grain structure. Trace portions 50 have acceptable medium size grain structure corresponding to the trace shown in FIG. 4A. Trace portion 51 is the result of heavy banding and trace portion 52 indicates mixed grain structure instead of solid banding appearing in trace portion 51. Whereas good, e.g., uniform large grain structure and banded areas have definite trace patterns, mixed grain structure, comprised of varying amounts of secondary grains more or less homogeneously dispersed in a background of coarsened primary grains, results in traces that are combinations of both good and banded grain structures. A good grain structure has reference to the magnetic properties of conventional grain oriented silicon steel and means general uniformity of grains exhibiting on average a permeability @ 10 oersteds ($\mu 10$) level in excess of 1800 while banded and mixed grain structures will be much lower.

The relative movement between the flux detecting head and the strip is essential to detecting a flux leakage. Without such relative movement no useful information will be revealed about grain size. In the preferred embodiment of the present invention described above, it can be seen that relative movement between the strip and the scanning head is the result of movement of the scanning head across the strip and the result of advancing movement of the strip between the payoff reel and coiler. For the present invention, the advancing strip speed is more significant in establishing flux leakage than the traversing speed.

Figure 5:
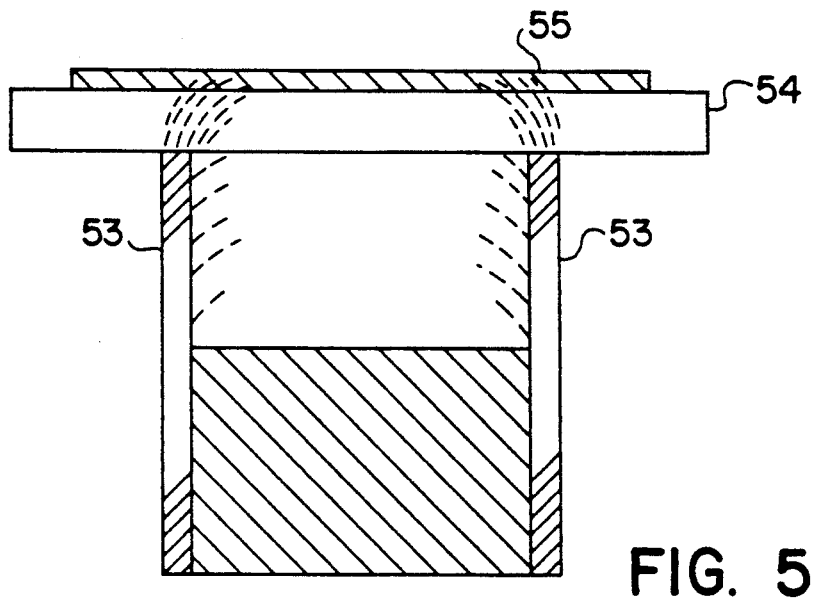
FIG. 5 is a diagram of the setup used to display grain pattern formations.
Figure 6A:
FIGS. 6A, 6B, 6C and 6D show the grain patterns obtained using the procedure shown in FIG. 5.
Figure 6B:
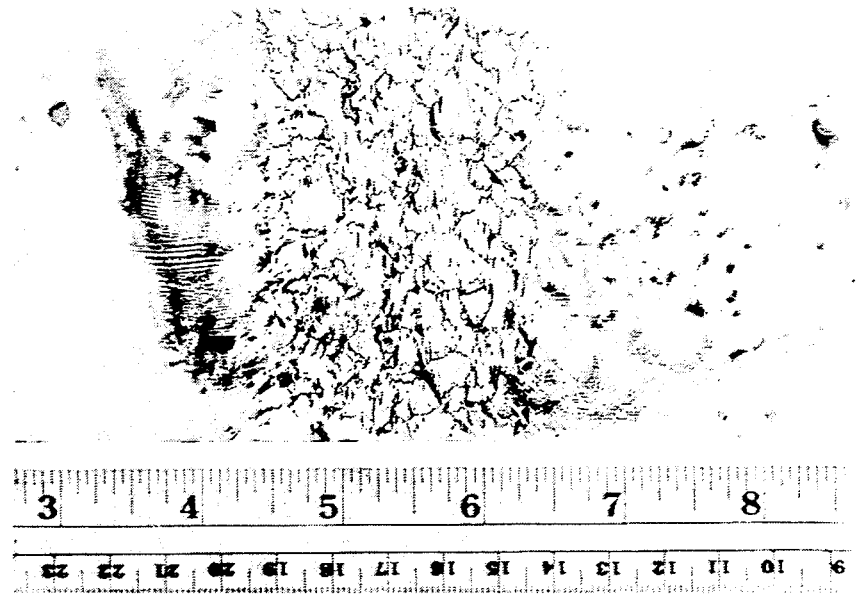
Figure 6C:
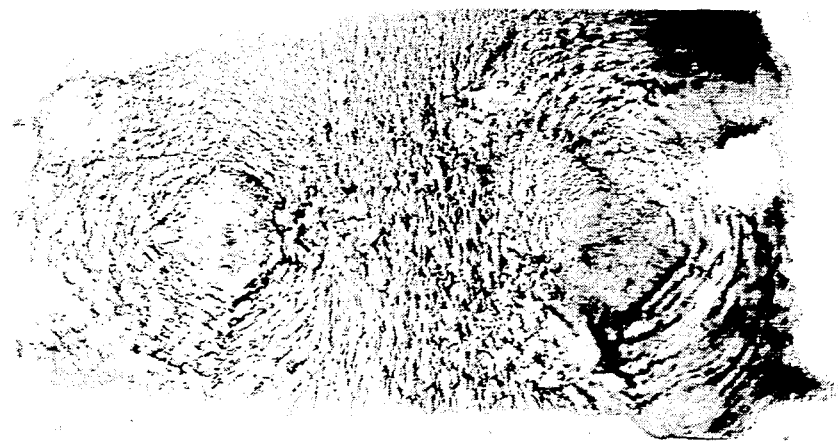
Figure 6D:
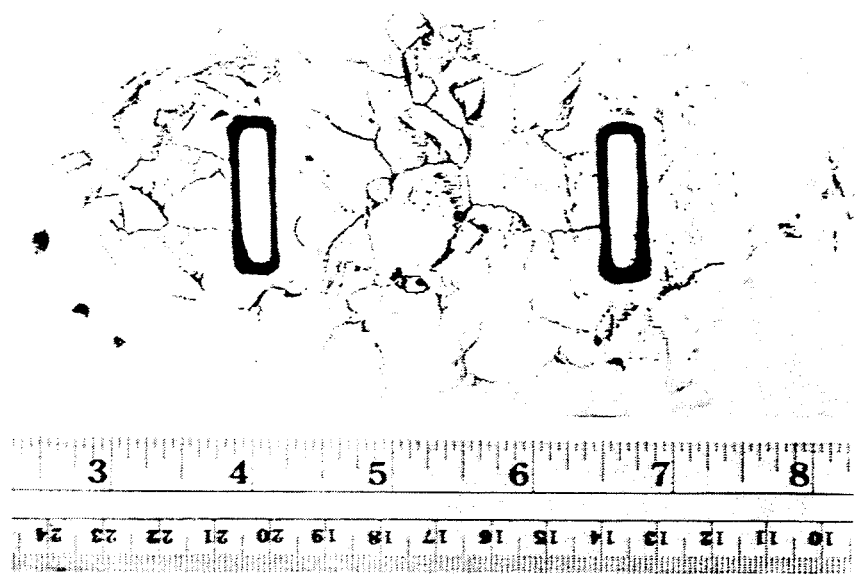

When performing magnetic tests, the focus of attention was only that amount of flux confined within the sample. However, the flux scanner senses any variations of flux that occur approximately $\frac{1}{8}$" above the test strip. In order to document the flux pattern at this distance from the strip, a $\frac{1}{8}$" wood spacer strip 54 was placed directly on the pole pieces 53 as shown in FIG. 5. Reference numeral 55 identifies a 3"×8" sample that was sprayed with flat white paint and allowed to dry. Various samples were prepared in this manner and placed singularly on the wood spacer 54. A small amount of imaging solution was deposited on the sample and allowed to dry under the influence of the magnetic field. Pictures of the grain patterns achieved by this process are shown in FIGS. 6A–6D. FIG. 6A shows the pattern from a sample with large grains and FIG. 6B from a medium grained sample which constituted a major portion of the total mults tested. FIG. 6C includes very small grains in the top portion of the picture while the bottom area is banded. FIG. 6D illustrates the result when the spacer strip 54 was eliminated whereby the test specimen comes to rest directly on the pole faces 53 during the test. The results indicate that flux linking the poles and confined within the sample between the poles leads to the development of components of leakage flux at the grain boundaries. According to the present invention, these components of flux are present and detectable by the magnetic pick-up head in a non-contacting fashion but in close proximity to the test strip surface as described herein.

The present invention has been designed to test grain oriented silicon steel strip on a process line operating at line speeds from 100 to 450 feet per minute and a speed of traverse movement by the scanning head 21 many times smaller through operation of drive motor 29, for example approximately 3 feet per minute. The orientation of the pole pieces 39 and 40 in relation to the directions of the strip movement is such that this flow of magnetic flux is parallel to the strip movement. Slight alterations of amplifier gain and pickup to test strip distance will broaden the speed range. The unit will operate with equal resolution if the permanent magnet is located above the test strip as in FIGS. 1, 2 and 3A or aligned below the test strip directly opposite the pickup head provided the alignment is maintained throughout the scanning process. With all components located on one side of the test strip only a single scan assembly is required and alignment is simple and fixed. Movement of the scanning head during the continuous scanning of the strip S takes the form of a zig zag path of the scanning track about the strip. The scanning head forms a very small acute attack angle with the side edge of the strip due to the relatively high velocity at which the strip travels along the pass line in relation to the simultaneous relative low velocity at which the scanning head moves transversely of the strip.

While the present invention has been described in connection with the preferred embodiments of the various figures, it is to be understood that other similar embodiments may be used or modifications and additions may be made to the described embodiment for performing the same function of the present invention without deviating therefrom. Therefore, the present invention should not be limited to any single embodiment, but rather construed in breadth and scope in accordance with the recitation of the appended claims.

We claim:

1. Apparatus for continuously testing the grain structure which can adversely affect the magnetic quality of an electrically conductive steel strip, said apparatus including the combination of:

means for inducing only a direct current magnetic flux field on one side of said steel strip to a detection site at that side of said steel strip without contacting the strip;

means for advancing said steel strip relative to said means for inducing a magnetic flux field, which field is parallel to the direction of strip advancement to allow continuous examination of the grain structure at diverse detection sites;

means for moving transversely across the width of said steel strip, said means for inducing a magnetic flux field; and means responsive to flux leakage at grain boundaries in the steel strip which leakage results from the relative advancing and transverse movement between said strip and responsive means for deriving an electrical signal indicative of the grain structure of the steel strip at selected detection sites established by the flux field without contacting the strip, said means responsive includes a magnetic pickup head oriented to define a pickup area having a length equal to or larger than a nominal grain size of the strip, the length oriented in a direction of strip movement.

2. The apparatus according to claim 1 wherein said means responsive to said flux leakage detects the magnitude of flux leakage.

3. The apparatus according to claim 1 wherein said means for moving include drive means for displacing said means for inducing transversely of said steel strip for continuous random sampling of the grain size thereof.

4. The apparatus according to claim 1 wherein said means for advancing comprise part of a strip processing line operating at a strip speed of between 100 and 450 feet per minute.

5. The apparatus according to claim 4 further including drive means for displacing said means for inducing transversely of said steel strip during continuous random sampling of the grain size thereof.

6. The apparatus according to claim 1 wherein said means for advancing said steel strip includes a coiler for said strip.

7. The apparatus according to claim 1 wherein said means for inducing a magnetic flux field includes permanent magnets and pole pieces for directing magnetic flux to said steel strip.

8. The apparatus according to claim 7 wherein said means responsive to said flux leakage includes a magnetic pickup head supported between said pole pieces.

9. The apparatus according to claim 8 further including means for supporting said pole pieces and said magnetic pickup head at a predetermined distance from the surface of one side of said steel strip.

10. The apparatus according to claim 8 wherein said magnetic pickup head has a width measured in the direction transverse to strip movement, which width is smaller than its length.

11. The apparatus according to claim 1 further including means for displaying the magnitude of electrical spikes which comprise said electrical signal.

12. The apparatus according to claim 1 further including means for recording said electrical signal.

13. A method for identifying banding and mixed grains in a grain oriented silicon steel strip, said method including the steps of:

inducing only a direct current magnetic flux field in said magnetic steel strip from one side of said steel strip without contacting the strip, causing relative movement between said magnetic flux field and the grain structure of the steel strip to allow continuous examination of the grain structure at diverse sites, said relative movement includes advancing said steel strip lengthwise relative to said flux field and transversing said flux field across the width of said steel strip, deriving an electrical signal corresponding in magnitude to flux leakage at grain boundaries from the same side of said steel strip without contacting the strip;

arranging a magnetic pickup head above said steel strip and orientating said magnetic pickup head so as to define a pickup area having a length equal to or greater than the nominal grain size of the strip, the length oriented in a direction of strip movement; and comparing the magnitude of the electrical signal represented by the flux leakage within areas of the steel strip having large grains as compared within areas of the steel strip having small grains to determine areas of banding and mixed grain structure.

14. The method according to claim 13 wherein said step of inducing said magnetic flux field includes forming a laminated arrangement of plate shaped permanent magnets and using pole pieces to direct the magnetic field to an impingement site with said magnetic steel strip.

15. The method according to claim 13 including the further step of detecting flux leakage in response to the induced magnetic flux field.

16. The method according to claim 15 wherein said step of causing relative movement includes moving said steel strip having an induced magnet flux field at a speed of between 100 and 450 feet per minute.

17. The method according to claim 15 wherein said step of causing relative movement includes moving the steel strip along a pass line at speeds of 100 feet per minute or greater while concurrently the magnetic flux field is moved at relatively slower speeds transversely to the moving strip.

18. The method according to claim 17 including the further step of recording said electric signal to form a visual display.

19. The method according to claim 13 wherein said width is defined by a gap in said magnetic pick up head.

* * * * *